US008729318B1

(12) United States Patent
Shuff et al.

(10) Patent No.: US 8,729,318 B1
(45) Date of Patent: May 20, 2014

(54) PROCESS FOR PRODUCING ETHANOL FROM METHYL ACETATE

(71) Applicant: Celanese International Corporation, Irving, TX (US)

(72) Inventors: Andrew Shuff, League City, TX (US); G. Paull Torrence, League City, TX (US); Brian Hokkanen, Houston, TX (US); Tianshu Pan, Houston, TX (US); Mark O. Scates, Houston, TX (US); Ronald D. Shaver, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/681,858

(22) Filed: Nov. 20, 2012

(51) Int. Cl.
*C07C 29/149* (2006.01)

(52) U.S. Cl.
USPC .......................................................... 568/885

(58) Field of Classification Search
USPC .......................................................... 568/885
See application file for complete search history.

(56) References Cited

U.S. PATENT DOCUMENTS

| | | |
|---|---|---|
| 2,591,671 A | 4/1952 | Catterall |
| 2,649,407 A | 8/1953 | Harrison et al. |
| 3,130,007 A | 4/1964 | Breck |
| 3,466,334 A | 9/1969 | Young et al. |
| 4,149,940 A | 4/1979 | Pinto |
| 4,454,358 A | 6/1984 | Kummer et al. |
| 4,481,146 A | 11/1984 | Leupold et al. |
| 4,497,967 A | 2/1985 | Wan |
| 4,521,630 A | 6/1985 | Wattimena et al. |
| 4,569,726 A | 2/1986 | Berg et al. |
| 4,754,074 A | 6/1988 | Hussmann |
| 4,758,600 A | 7/1988 | Arimitsu et al. |
| 4,843,170 A | 6/1989 | Isshiki et al. |
| 5,004,845 A | 4/1991 | Bradley et al. |
| 5,061,671 A | 10/1991 | Kitson et al. |
| 5,124,004 A | 6/1992 | Grethlein et al. |
| 5,162,578 A | 11/1992 | McCain, Jr. et al. |
| 5,292,916 A | 3/1994 | Matsuzaki et al. |
| 5,565,068 A | 10/1996 | Parker et al. |
| 5,770,761 A | 6/1998 | Lin et al. |
| 6,339,171 B1 | 1/2002 | Singh et al. |
| 6,472,555 B2 | 10/2002 | Choudary et al. |
| 6,693,213 B1 | 2/2004 | Kolena et al. |
| 6,713,655 B2 | 3/2004 | Yilmaz et al. |
| 6,723,886 B2 | 4/2004 | Allison et al. |
| 6,852,877 B1 | 2/2005 | Zeyss et al. |
| 6,933,414 B1 | 8/2005 | Stauffer |
| 7,091,155 B2 | 8/2006 | Inui et al. |
| 7,115,772 B2 | 10/2006 | Picard et al. |
| 7,148,390 B2 | 12/2006 | Zhou et al. |
| 7,351,559 B2 | 4/2008 | Verser et al. |
| 7,608,744 B1 | 10/2009 | Johnston et al. |
| 7,744,727 B2 | 6/2010 | Blum et al. |
| 7,834,223 B2 | 11/2010 | Atkins et al. |
| 7,884,253 B2 | 2/2011 | Stites et al. |
| 7,906,680 B2 | 3/2011 | Scates et al. |
| 7,964,379 B2 | 6/2011 | Verser et al. |
| 8,080,693 B2 | 12/2011 | Chornet et al. |
| 8,088,832 B2 | 1/2012 | Melnichuk et al. |
| 8,143,444 B2 | 3/2012 | Mariansky et al. |
| 8,173,324 B2 | 5/2012 | Fisher et al. |
| 8,211,821 B2 | 7/2012 | Weiner et al. |
| 8,222,466 B2 | 7/2012 | Horton et al. |
| 8,304,586 B2 | 11/2012 | Jevtic et al. |
| 8,309,782 B2 | 11/2012 | Le Peltier et al. |
| 2004/0242917 A1 | 12/2004 | Inui et al. |
| 2004/0267074 A1 | 12/2004 | Grosso et al. |
| 2005/0028435 A1 | 2/2005 | Pace et al. |
| 2005/0181940 A1 | 8/2005 | Wang et al. |
| 2008/0319236 A1 | 12/2008 | McNeff et al. |
| 2009/0166172 A1 | 7/2009 | Casey |
| 2009/0209786 A1 | 8/2009 | Scates et al. |
| 2009/0259086 A1 | 10/2009 | Bailey et al. |
| 2009/0264285 A1 | 10/2009 | Luo et al. |
| 2010/0261800 A1 | 10/2010 | Daniel et al. |
| 2011/0060169 A1 | 3/2011 | Kaizik et al. |
| 2011/0124927 A1 | 5/2011 | Stites et al. |

FOREIGN PATENT DOCUMENTS

| | | |
|---|---|---|
| EP | 2060553 | 5/2009 |
| EP | 2072488 | 6/2009 |

OTHER PUBLICATIONS

Perry, et al. "Perry's Chemical Engineers Handbook", 7th Ed. (1997) pp. 22-37 and 22-69.

*Primary Examiner* — Elvis O Price

(57) ABSTRACT

The present invention relates to a process for producing ethanol by methyl acetate hydrogenolysis. The process comprises the step of reacting carbon monoxide and methanol in a reaction medium to form a reaction solution that comprises acetic acid and from 0.5 to 25 wt. % methyl acetate. The process further comprises the step of esterifying the acetic acid and feeding the methyl acetate to a distillation column to remove alkyl halides. The process further comprises the steps of reacting the methyl acetate stream that does not contain alkyl halides and hydrogen in the presence of a second catalyst to form an alcohol product that comprises ethanol and/or methanol.

21 Claims, 4 Drawing Sheets

PROCESS FOR PRODUCING ETHANOL FROM METHYL ACETATE

FIELD OF THE INVENTION

The present invention relates generally to alcohol production processes and, in particular, to ethanol production processes that use carbonylation processes to produce methyl acetate as an intermediate to form ethanol.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are often formed with ethanol or are formed in side reactions. These impurities may limit the production of ethanol and may require expensive and complex purification trains to separate the impurities from the ethanol.

For example, U.S. Pat. No. 7,884,253 discloses methods and apparatuses for selectively producing ethanol from syngas. The syngas is derived from cellulosic biomass (or other sources) and can be catalytically converted into methanol, which in turn can be catalytically converted into acetic acid or acetates. The ethanoic acid product may be removed from the reactor by withdrawing liquid reaction composition and separating the ethanoic acid product by one or more flash and/or fractional distillation stages from the other components of the liquid reaction composition such as iridium catalyst, ruthenium and/or osmium and/or indium promoter, methyl iodide, water and unconsumed reactants which may be recycled to the reactor to maintain their concentrations in the liquid reaction composition. As another example, EP2060553 discloses a process for the conversion of a carbonaceous feedstock to ethanol wherein the carbonaceous feedstock is first converted to ethanoic acid, which is then hydrogenated and converted into ethanol. Also, U.S. Pat. No. 4,497,967 discloses an integrated process for the preparation of ethanol from methanol, carbon monoxide and hydrogen feedstock. The process esterifies an acetic anhydride intermediate to form ethyl acetate and/or ethanol. In addition, U.S. Pat. No. 7,351,559 discloses a process for producing ethanol including a combination of biochemical and synthetic conversions results in high yield ethanol production with concurrent production of high value co-products. An acetic acid intermediate is produced from carbohydrates, such as corn, using enzymatic milling and fermentation steps, followed by conversion of the acetic acid into ethanol using esterification and hydrogenation reactions. Also, U.S. Pub. No. 2010/0261800 discloses a process for the production of ethanol of ethanol from synthesis gas through methanol carbonylation to form ethanoic acid and esterifing ethanoic acid to methyl ethanoate and/or ethyl ethanoate.

In additional to alkanoic acids, methyl acetate can also be used to make ethanol. For example, U.S. Pat. No. 8,088,832 discloses a method and apparatus for synthesizing ethanol using stepwise catalytic reaction to convert carbon monoxide and hydrogen into ethanol through intermediates, such as methanol and methanol acetate, using catalysts including iridium acetate. U.S. Pat. No. 8,080,693 discloses a process for converting methanol to ethanol which comprises reacting methanol and carbon monoxide in the presence of a catalyst to produce a product comprising at least 25 mole % methyl acetate and, in some instances, acetic acid. U.S. Pat. No. 4,454,358 discloses a process for continuously producing ethanol via the carbonylation of methanol and hydrogenating a mixture of methanol and methyl acetate to form ethanol. Another route to ethanol is proposed by U.S. Pub. No. 2011/0124927 for converting syngas to dimethyl ether, carbonylating the dimethyl ether to methyl acetate, hydrogenating the methyl acetate to methanol and ethanol, and recovering the ethanol product.

In view of the conventional processes and literature, the need remains for improved ethanol production processes that are capable of effectively using methyl acetate, which may be formed from methanol and/or carbon monoxide feed sources.

SUMMARY OF THE INVENTION

In one embodiment, the present invention relates to a process for producing ethanol by hydrogenolysis of methyl acetate. The process comprises the step of reacting carbon monoxide and methanol in a reaction medium to form a reaction solution that comprises acetic acid and from 0.5 to 25 wt. % methyl acetate. In one embodiment, the reaction medium comprises water, acetic acid, methyl acetate, a first catalyst, and an alkyl halide. The process further comprises the steps of flashing the reaction solution to yield a carbonylation product and a liquid catalyst recycle stream, separating the carbonylation product into a first methyl acetate stream and acetic acid stream, and esterifying the acetic acid stream to form a second methyl acetate stream. The process further comprises the steps of feeding the first methyl acetate stream and the second methyl acetate stream to a distillation column to remove alkyl halides and obtain a third methyl acetate stream and reacting the third methyl acetate stream and hydrogen in the presence of a second catalyst to form an alcohol product that comprises ethanol and methanol. The process further comprises the steps of recovering ethanol from the alcohol product. Preferably, the third methyl acetate stream comprises at least 60 wt. % methyl acetate, less than 5 wt. % acetic acid, and is substantially free of methyl iodide. Preferably, the first methyl acetate stream comprises at least 20 wt. % methyl acetate and the second methyl acetate stream comprises at least 50 wt. % methyl acetate, less than 5 wt. % acetic acid and less than 2 wt. % water.

The process further comprises the step of withdrawing the acetic acid as a sidedraw. Preferably, the sidedraw comprises at least 30 wt. % acetic acid, less than 10 wt. % methyl acetate, and less than 0.1 wt. % alkyl halide.

The process further comprises the steps of esterifying the acetic acid stream with methanol in a reactive distillation column and separating a water stream from the reactive distillation column.

In another embodiment, the process comprises the step of esterifying the carbonylation product to form a methyl acetate enriched stream.

In another embodiment, the process further comprises the step of separating the carbonylation product into an acetic acid stream and a first overhead stream comprising methyl acetate, acetaldehyde, and alkyl halide. The process further comprises the step of separating the first overhead stream into a methyl acetate residue and a second overhead stream comprising acetaldehyde and alkyl halide. The process further comprises the step of extracting the second overhead stream with an aqueous stream to obtain a raffinate comprising alkyl halide and an extractant comprising acetaldehyde. The process further comprises the step of combining the methyl acetate residue and extractant to form a feed stream. The process further comprises the step of esterifying the acetic acid stream to form a methyl acetate stream and introducing the methyl acetate stream with the first overhead stream prior to separation. The process further comprises the step of reacting the feed stream and hydrogen in the presence of a second catalyst to form an alcohol product that comprises ethanol and methanol. Preferably, the ratio between ethanol and methanol is greater than 50%.

In another embodiment, the process comprises the step of extracting the second overhead stream with an alkane to obtain a raffinate comprising acetaldehyde and an extractant comprising the alkyl halide and alkane. The process further comprises the step of combining the methyl acetate residue and raffinate to form a feed stream. The process further comprises the steps of reacting the feed stream and hydrogen in the presence of a second catalyst to form an alcohol product that comprises ethanol and methanol and recovering ethanol from the alcohol product.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
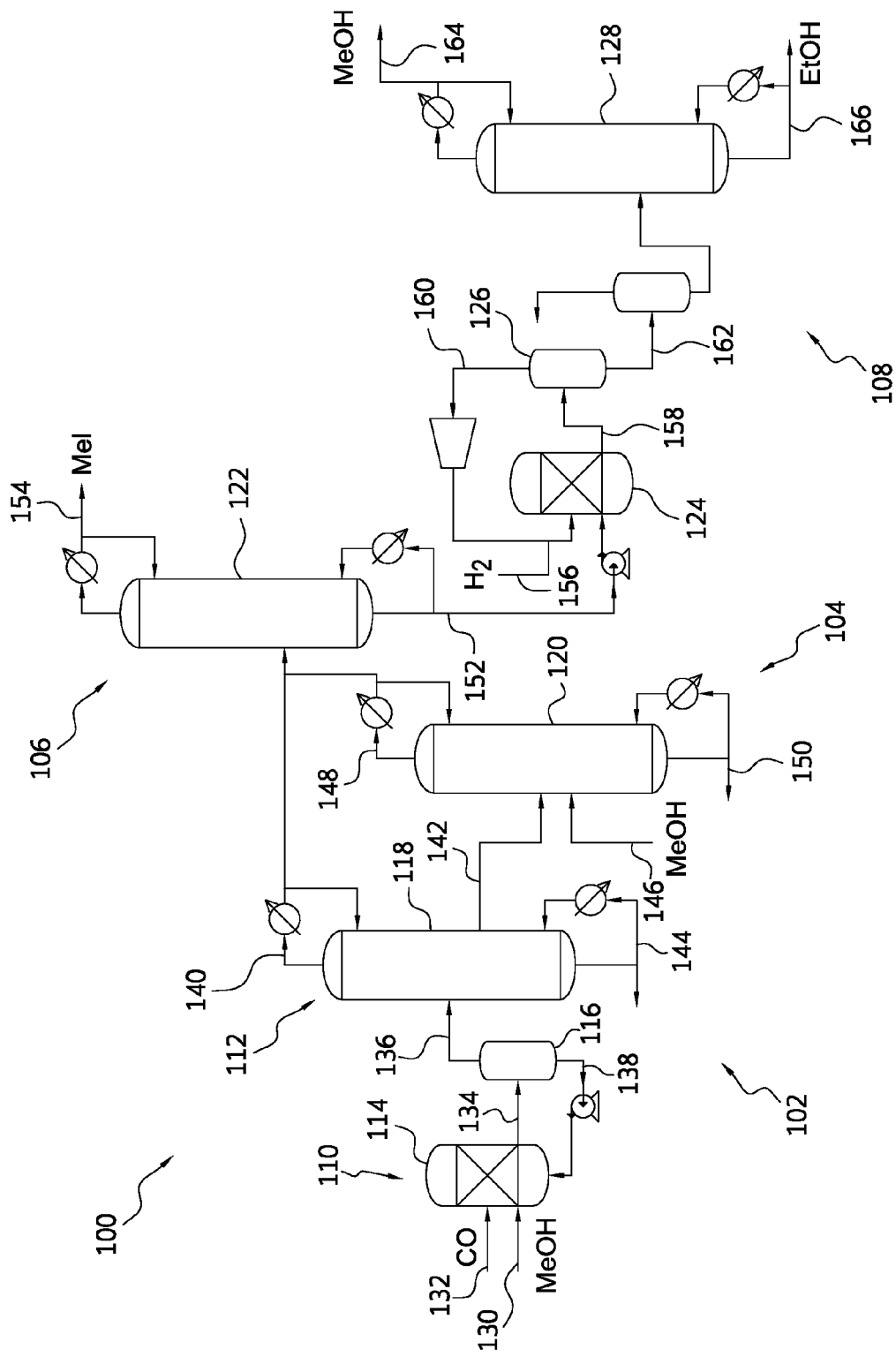
FIG. 1 is a schematic diagram of an ethanol production process in accordance with one embodiment of the present invention.

In general, the present invention relates to processes for making ethanol through an intermediate methyl acetate. In one embodiment, the invention is a process for producing ethanol comprising the steps of reacting methyl acetate, under hydrogenolysis conditions, with hydrogen to form methanol and ethanol. The methyl acetate is formed by carbonylation of methanol using alkyl halides, such as halogen promoters, e.g., methyl iodide (MeI). During the carbonylation reaction acetic acid is also formed. In order to increase the amount of methyl acetate to maximize the amount of ethanol being made, the acetic acid may be separated from the reaction mixture and esterified to form additional methyl acetate. As a result of using alkyl halides in the carbonylation reaction, the methyl acetate streams may comprise a small amount of alkyl halides. Embodiments of the present invention provide a method to remove the alkyl halides, such that an alkyl halide-free methyl acetate stream may be used for the hydrogenolysis reaction to form ethanol.

In one embodiment, due to the reaction conditions and reaction medium of the carbonylation reaction, permanganate reducing compounds (PRC's) are also formed as side products. PRC's may be recovered and combined with the methyl acetate stream to undergo reduction to form ethanol. However, when recovering PRC's from the carbonylation reaction mixture, the alkyl halides may pass through into the stream and as such, the resulting PRC's stream may comprise the alkyl halides. Embodiments of the present invention advantageously increase the amounts of alkyl halides that can be removed from the PRC's stream to yield an alkyl halide-free PRC's stream, which may be combined with the alkyl halide-free methyl acetate.

In one embodiment, alkyl halides may be removed from the PRC's stream by using an aqueous solvent or an organic solvent. The use of an aqueous solvent may increase the amount of water in the resulting ethanol product and a drying column may be used to remove water from the ethanol. In one embodiment, an alkane may be used as the organic solvent to remove alkyl halides from the PRC's stream.

Accordingly, the present invention, in one embodiment, relates to a process for producing ethanol by methyl acetate hydrogenolysis. The process comprises the step of reacting carbon monoxide and methanol in a reaction medium to form a reaction solution. The reaction medium comprises water, acetic acid, methyl acetate, a first catalyst and an alkyl halide. The reaction solution comprises acetic acid, methyl acetate, water, and alkyl halide. The reaction solution comprises acetic acid in an amount from 1 to 40 wt. %, e.g., from 2 to 35 wt. %, or from 3 to 30 wt. %. In one embodiment, the reaction solution comprises methyl acetate in an amount from 0.5 to 25 wt. %, e.g., from 5 to 25 wt. % or from 10 to 24.9 wt. %.

The process further comprises the step of flashing the reaction solution to yield a carbonylation product and a liquid catalyst recycle stream. In one embodiment, a portion of the acetic acid may be removed in the liquid catalyst recycle stream. The liquid catalyst recycle stream may also comprise methyl acetate. The carbonylation product comprises acetic acid, methyl acetate, water and alkyl halides. The carbonylation product comprises acetic acid in an amount greater than 15 wt. %, e.g., greater than 20 wt. %. In terms of ranges the acetic acid concentration in the carbonylation product may range from 15 to 50 wt. %, e.g., from 20 to 50 wt. %. In addition, the carbonylation product comprises methyl acetate in an amount from 10 wt. % to 45 wt. %, e.g., from 15 wt. % to 40 wt. % and from 20 wt. % to 35 wt. %.

The process further comprises the step of separating the carbonylation product into a first methyl acetate stream and an acetic acid stream. In one embodiment, the acetic acid stream is a sidedraw from a distillation column. The sidedraw comprises at least 30 wt. % acetic acid, e.g., at least 40 wt. %, or at least 50 wt. %. The sidedraw comprises less than 10 wt. % methyl acetate, less than 8 wt. %, or less than 6 wt. %. The sidedraw comprises less than 0.1 wt. % alkyl halide, e.g., less than 0.05 wt. %, or less than 0.01 wt. %. In one embodiment, the first methyl acetate stream comprises methyl acetate and alkyl halide. The first methyl acetate stream comprises at least 20 wt. % methyl acetate, e.g., at least 35 wt. %, or at least 40 wt. %. The first methyl acetate stream comprises at least 10 wt. % alky halide, e.g., at least 15 wt. %, or at least 25 wt. %.

The process further comprises the step of esterifying the acetic acid stream to form a second methyl acetate stream. In one embodiment, the esterification of acetic acid stream is conducted in an esterification unit, e.g., a reactive distillation column, with methanol to form an esterified product. In one embodiment, an excess amount of methanol is used in the esterification unit to convert most of the acetic acid to methyl acetate. The excess methanol may be recovered and directed to the carbonylation reactor or back to the esterification reactor. The esterified product comprises less than 5 wt. % acetic acid, e.g., less than 1 wt. %, or less than 0.1 wt. %. The esterified product may be separated into a second methyl acetate stream and an aqueous stream. The second methyl acetate stream comprises at least 50 wt. % methyl acetate, e.g., at least 60 wt. %, or at least 75 wt. %. The second methyl acetate stream comprises less than 1 wt. % water, e.g., less than 0.1 wt. %, or less than 0.01 wt. %. The second methyl acetate stream comprises less than 50 wt. % methanol, e.g., less than 30 wt. %, or less than 25 wt. %. The second methyl acetate stream is substantially free of acetic acid, e.g., less than 1 wt. %, e.g., less than 0.1 wt. %, or less than 0.01 wt. %. In one embodiment, most of the acetic acid is reacted to form methyl acetate. Any unreacted acetic acid is removed in the aqueous stream. The aqueous stream comprises less than 10 wt. % acetic acid, e.g., less than 5 wt. %, or less than 3 wt. %. The aqueous stream comprises at least 80 wt. % water, e.g., at least 90 wt. %, or at least 95 wt. %.

The process further comprises the step of feeding the first methyl acetate and the second methyl acetate stream to a distillation column to remove alkyl halides and to obtain a third methyl acetate stream. The removal of alkyl halide from the methyl acetate stream is beneficial because (1) the alkyl halide may be recycled to the carbonylation reaction, and (2) alkyl halides may be detrimental to the hydrogenolysis reaction. Therefore, the removal of alkyl halides may yield a purified third methyl acetate stream that is a more suitable feed to a hydrogenolysis process for the production of methanol and/or ethanol. In one embodiment, the first methyl acetate stream and the second methyl acetate stream may be fed separately to the distillation column. In another embodiment, the first methyl acetate stream may be combined with the second methyl acetate stream and fed to the distillation column to yield a third methyl acetate stream. The third methyl acetate stream comprises at least 60 wt. % methyl acetate, e.g., at least 70 wt. %, or at least 80 wt. %. The third methyl acetate stream may also comprise unreacted methanol from the esterification reaction. The third methyl acetate stream comprises less than 30 wt. % methanol, e.g., less than 20 wt. %, or less than 10 wt. %. The third methyl acetate stream is substantially free of alkyl halides, e.g., less than 0.01 wt. %, or less than 0.001 wt. %.

The process further comprises the step of reacting the third methyl acetate stream and hydrogen in the presence of a second catalyst to form an alcohol product that comprises ethanol and methanol. The hydrogenolysis reaction may take place in the presence of a suitable hydrogenolysis catalyst. Examples of hydrogenolysis catalysts include copper containing catalysts, especially those with copper in a reduced or partially reduced state. Examples of such copper containing catalysts are described in U.S. Pat. Nos. 5,198,592; 5,414,161; and 7,947,746; U.S. Pub. No. 2009/0326080, and WO83/03409, the entireties of which are incorporated herein by reference.

After methanol and ethanol are produced by hydrogenolysis, the methanol and ethanol may be separated by a suitable separation technique, such as distillation, to form an ethanol stream and a methanol stream. The ethanol stream comprises at least 88 wt. % ethanol, e.g., at least 90 wt. %, or at least 93 wt. %. The methanol stream comprises at least 60 wt. % methanol, e.g., at least 70 wt. %, or at least 80 wt. %. In one embodiment, the methanol stream, when enriched in methanol, may be fed in whole or part to the carbonylation reactor and/or esterification reactor. In one embodiment, the methanol stream comprises methanol and methyl acetate. The methanol stream may be recycled to the esterification step to generate additional methyl acetate. The amount of methyl acetate, when present, may be less than 30 wt. %, e.g., less than 20 wt. % or less than 15 wt. %.

In another embodiment, the carbonylation product is fed directly to the esterification unit with methanol to form methyl acetate prior to separating the carbonylation product. By eliminating the separation, the acetic acid may be sent to the esterification unit in the vapor phase.

As stated above, the methyl acetate streams are fed to a distillation column to remove alkyl halides. In addition to alkyl halides, methyl acetate and PRC's are present in the alkyl halides stream and the methyl acetate and PRC's may be recovered and fed to the hydrogenolysis reactor to form ethanol. In another embodiment, the PRC's may be recovered with a PRC recovery system (PRS) that comprises one or more distillation column. PRC's, may include acetaldehyde, acetone, methyl ethyl ketone, butyraldehyde, crotonaldehyde, 2-ethyl crotonaldehyde, 2-ethyl butyraldehyde, the aldol condensation products thereof, or mixtures thereof. Exemplary PRS include those described in U.S. Pat. Nos. 7,855,306; 7,223,886; 7,855,306; 6,143,930 and 6,339,171, and U.S. Pub. No. 2012/0090981, the entire contents and disclosures of which is hereby incorporated by reference. A stream enriched with PRC's may be separated from the carbonylation production process and introduced to the PRS. This stream may also comprise alkyl halides.

Although it is preferred to recover methyl iodide for returning to the carbonylation reactor, other alkyl halides such as ethyl iodide, propyl iodide, butyl iodide, pentyl iodide, hexyl iodide, and isomers thereof, may also be removed from the treated streams of the PRS. The alkyl halides, including halogen promoters, may cause corrosion in the system by forming hydroiodic (HI) acid in distillation portions of the PRS as described in several reactions that involve the halogen promoter, methyl iodide.

In one embodiment, one or more distillation columns are used to recover PRC's. The alkyl halides stream is fed to a distillation column to form a vapor phase stream overhead, a higher boiling liquid phase residuum, and a sidestream. The vapor phase stream overhead is enriched with PRC's with respect to the alkyl halides stream. The sidestream is enriched with methyl acetate with respect to the alkyl halides stream. The sidestream may be in vapor phase and may be fed directly to the hydrogenolysis reactor. The vapor phase stream may be condensed and extracted with an aqueous solvent, i.e., water, to obtain an aqueous stream comprising an aqueous PRC's stream and a raffinate comprising methyl iodide.

In another embodiment, the vapor phase stream may be condensed an extracted with an organic solvent, e.g., alkane, to obtain an organic stream comprising methyl iodide and a raffinate comprising the PRC's. The PRC's may be combined with the methyl acetate stream and fed to the hydrogenolysis reactor.

In one embodiment, methyl acetate may be in liquid form and required to be vaporized prior to being fed to the hydrogenolysis reactor. In another embodiment, the methyl acetate stream may be in vapor phase and the purified liquid PRC's may be vaporized by combining with the vapor methyl acetate streams. As such a vaporizer may not be needed.

Carbonylation

The raw materials, methanol and hydrogen, used in connection with the process of this invention may be derived from any suitable source including natural gas, petroleum, coal, biomass, and so forth. For purposes of the present invention, acetic acid and methyl acetate may be produced using a methanol feed via methanol carbonylation as described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. In one embodiment, the production of ethanol is integrated with such methanol carbonylation processes that form mixtures of acetic acid and methyl acetate.

As petroleum and natural gas prices fluctuate becoming either more or less expensive, methods for producing acetic acid, and methyl acetate and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid and/or methyl acetate. In a similar manner, hydrogen for the hydrogenolysis step may be supplied from syngas.

In some embodiments, some or all of the raw materials for the above-described carbonylation process may be derived partially or entirely from syngas. For example, the acetic acid and/or methyl acetate may be formed from methanol and carbon monoxide, both of which may be derived from syngas. The syngas may be formed by partial oxidation reforming or steam reforming, and the carbon monoxide may be separated from syngas. Similarly, hydrogen that is used in the step of methyl acetate hydrogenolysis to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Black liquor, which is an aqueous solution of lignin residues, hemicellulose, and inorganic chemicals, may also be used as a biomass source. Biomass-derived syngas has a detectable $^{14}C$ isotope content as compared to fossil fuels such as coal or natural gas.

Although carbonylation may be a preferred acetic acid and methyl acetate production method, other suitable methods may be employed. In a preferred embodiment that employs carbonylation, the carbonylation system preferably comprises a reaction zone, which includes a reactor, a flasher and optionally a reactor recovery unit. In one embodiment, carbon monoxide is reacted with methanol in a suitable reactor, e.g., a continuous stirred tank reactor ("CSTR") or a bubble column reactor. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

The carbonylation reaction may be conducted in a homogeneous catalytic reaction system comprising a reaction solvent, methanol and/or reactive derivatives thereof, a Group VIII catalyst, at least a finite concentration of water, and optionally an iodide salt.

Suitable catalysts include Group VIII catalysts, e.g., rhodium and/or iridium catalysts. The rhodium catalyst may be added in any suitable form such that the active rhodium catalyst is a carbonyl iodide complex. Exemplary rhodium catalysts are described in Michael Gauβ, et al., *Applied Homogeneous Catalysis with Organometallic Compounds: A Comprehensive Handbook in Two Volume*, Chapter 2.1, p. 27-200, ($1^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, a catalyst co-promoter comprising lithium iodide, lithium acetate, or mixtures thereof may be employed. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6,000 ppm. The carbonylation of methanol utilizing iridium catalyst is well known and is generally described in U.S. Pat. Nos. 5,942,460; 5,932,764; 5,883,295; 5,877,348; 5,877,347; and 5,696,284, which are hereby incorporated by reference.

A halogen co-catalyst/promoter is generally used in combination with the Group VIII metal catalyst component. Methyl iodide is a preferred halogen promoter. Preferably, the concentration of halogen promoter in the reaction medium ranges from 1 wt. % to 50 wt. %, and preferably from 2 wt. % to 30 wt. %.

The halogen promoter may be combined with the salt stabilizer/co-promoter compound. Particularly preferred are iodide or acetate salts, e.g., lithium iodide or lithium acetate.

Other promoters and co-promoters may be used as part of the catalytic system of the present invention as described in U.S. Pat. No. 5,877,348, which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 wppm.

In one embodiment, the temperature of the carbonylation reaction in the reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa. Acetic acid and methyl acetate are typically manufactured in a liquid phase reaction at a temperature from 150° C. to 200° C. and a total pressure from 2 to 5 MPa.

In one embodiment, reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid and methyl acetate.

Water may be formed in situ in the reaction medium, for example, by the esterification reaction between methanol reactant and acetic acid product. In some embodiments, water is introduced to reactor together with or separately from other components of the reaction medium. Water may be separated from the other components of reaction product withdrawn from reactor and may be recycled in controlled amounts to maintain the required concentration of water in the reaction medium. Preferably, the concentration of water maintained in the reaction medium ranges from 0.1 wt. % to 16 wt. %, e.g., from 1 wt. % to 14 wt. %, or from 1 wt. % to 3 wt. % of the total weight of the reaction product.

The desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt % to 30 wt. %, e.g., from 1 wt. % to 25 wt. %, or from 2 wt. % to 20 wt. %; and the lithium iodide may be present in amounts ranging from 5 wt. % to 20 wt %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500.

Esterification

According to embodiments of the present invention, the acetic acid present in the acetic acid stream is reacted with an alcohol stream, e.g., comprising methanol, in an esterification unit to produce methyl acetate and water. The methyl acetate is reacted with hydrogen in a hydrogenolysis reactor to form ethanol and methanol.

An esterification unit of the present invention comprises a reaction zone and a separation zone. In some embodiments, an esterification unit comprises a reactor coupled to one or more distillation columns. In other embodiments, the esterification unit comprises a reactive distillation column (also referred to herein as the second column) comprising a reaction section and a distillation section, to produce a distillate stream comprising methyl acetate and a residue stream comprising water.

As indicated above, acetic acid from the acetic acid stream is reacted with methanol to form methyl acetate. The methanol is preferably fed to the esterification unit in a counter-current flow to the acetic acid stream to facilitate the production of methyl acetate. The process parameters for the esterification step may vary widely depending, for example, on the catalyst employed and the ester being formed.

Hydrogenolysis

As discussed above, the processes of the invention involve a step of subjecting methyl acetate to hydrogenolysis in a hydrogenolysis reactor to form methanol and ethanol. In this context, the term "hydrogenolysis" of methyl acetate refers to the reaction of methyl acetate with hydrogen to form methanol and ethanol, but it should be understood that this reaction is not limited to any particular mechanism and may occur via one or more intermediates, e.g., acetic acid, which may undergo further reaction, e.g., hydrogenation, to form one or more alcohol species, e.g., ethanol.

The invention may be described in relation to the production of ethanol, but, as indicated above, methanol is coproduced. At least a portion of the methanol produced preferably is recycled to the process for producing acetic acid in the carbonylation reaction or to the process of producing methyl acetate in the esterifying unit. Additionally or alternatively, at least a portion of the methanol may be recovered as a saleable end product.

In embodiments where at least a portion of the methanol is recycled to carbonylation reaction or esterification reaction, at least a portion of any methanol stream may be treated in one or more purification steps, prior to being introduced into the reaction zone for synthesis of acetic acid or methyl acetate.

The hydrogenolysis step may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor, provided with a heat transfer medium, may be used. In many cases, the reaction zone may be housed in a single vessel or in a series of vessels with heat exchangers therebetween.

The catalyst may be employed in a fixed bed reactor, e.g., in the shape of a pipe or tube, where the reactants, typically in the vapor form, are passed over or through the catalyst. Other reactors, such as fluid or ebullient bed reactors, may be employed. In some instances, the hydrogenolysis catalysts may be used in conjunction with an inert material to regulate the pressure drop of the reactant stream through the catalyst bed and the contact time of the reactant compounds with the catalyst particles.

Contact or residence time may also vary widely, depending upon such variables as amount of methyl acetate, catalyst, reactor, temperature, and pressure. Typical contact times range from a fraction of a second to more than several hours when a catalyst system other than a fixed bed is used. Contact times, at least for vapor phase reactions, may be from 0.1 to 100 seconds.

The hydrogenolysis of methyl acetate to form methanol and ethanol is preferably conducted in the presence of a hydrogenolysis catalyst. Suitable hydrogenolysis catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA.

Particularly useful hydrogenolysis catalysts include copper containing catalysts. These copper containing catalysts may further comprise one or more additional metals, optionally, on a catalyst support. The optional additional metal or metals may be selected from Group IB, IIB, IIIB, IVB, VB, VIIB, VIIB, VIII transition metals, a lanthanide metal, an actinide metal or a metal selected from any of Groups IIIA, WA, VA, and VIA. Particular metal combinations for some exemplary catalyst compositions include copper/cobalt/zinc, copper/zinc/iron, copper/cobalt/zinc/iron, copper/cobalt/zinc/iron/calcium, and copper/cobalt/zinc/molybdenum/sodium. Particular copper containing catalysts may comprise copper chromite, copper and zinc, and/or copper-zinc-oxide. Exemplary catalysts are further described in U.S. Pat. Nos. 5,198,592; 5,414,161; and 7,947,746; U.S. Pub. No. 2009/0326080, and WO83/03409, the entireties of which are incorporated herein by reference. Hydrogenolysis catalysts may comprise CuO or ZnO. However, CuO and ZnO may be reduced or partially reduced by hydrogen during the course of the hydrogenolysis reaction. It is also possible to pre-reduce CuO and/or ZnO by passing hydrogen over the catalyst before the introduction of the methyl acetate feed.

As indicated above, in some embodiments, the catalyst further comprises at least one additional metal, which may function as a promoter.

In addition to one or more metals, in some embodiments of the present invention the catalysts further comprise a support or a modified support. As used herein, the term "modified support" refers to a support that includes a support material and a support modifier, which adjusts the acidity of the support material.

In particular, the hydrogenolysis of methyl acetate may achieve favorable conversion of methyl acetate and favorable selectivity and productivity to methanol and ethanol. For purposes of the present invention, the term "conversion" refers to the amount of methyl acetate in the feed that is converted to a compound other than methyl acetate. Conversion is expressed as a mole percentage based on methyl acetate in the feed. The conversion may be at least 75%, e.g., at least 85%, or at least 90%. Although catalysts that have high conversions are desirable, such as at least 95% or at least 97%, in some embodiments a low conversion may be acceptable at high selectivity for methanol/ethanol. It is, of course, well understood that in many cases, it is possible to compensate for conversion by appropriate recycle streams or use of larger reactors, but it is more difficult to compensate for poor selectivity.

Selectivity is expressed as a percentage of moles of product per moles of converted methyl acetate. It should be understood that each compound converted from methyl acetate has an independent selectivity and that selectivity is independent from conversion. Generally, methanol and ethanol will be produced in equal molar ratios. The catalyst selectivity to each product, i.e., methanol and ethanol, may be at least 70%, e.g., at least 80%, or at least 90%. Preferred embodiments of the hydrogenolysis process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the methyl acetate passed over the catalyst is converted to alkanes, which have little value other than as fuel.

The term "productivity," as used herein, refers to the grams of a specified product, e.g., ethanol, formed during the hydrogenolysis based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is possible. In terms of ranges, the productivity may be from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude alcohol product produced by the hydrogenolysis process, before any subsequent processing, such as purification and separation, will typically comprise methanol, ethanol and, possibly, water. The product stream from the hydrogenolysis reaction zone may also comprise unconverted methyl acetate. This unconverted methyl acetate may be separated from methanol and ethanol and saponified, for example, at room temperature with caustic on a stoichiometric basis. When aqueous sodium hydroxide is used as the caustic, the saponification product will comprise sodium acetate in aqueous solution. Caustic may be recovered, for example, by using a bipolar membrane. Sodium acetate may be converted to acetic acid by adjustment of pH. Caustic may be recycled to the saponification reaction zone. Acetic acid may be recycled to a reaction zone for converting acetic acid into vinyl acetate, which may be in turn polymerized.

The ethanol product produced by the process of the present invention may be an industrial grade ethanol comprising from 75 to 96 wt. % ethanol, e.g., from 80 to 96 wt. % or from 85 to 96 wt. % ethanol, based on the total weight of the ethanol product.

The finished ethanol composition of the present invention preferably contains very low amounts, e.g., less than 0.5 wt.

%, of other alcohols, such as methanol, butanol, isobutanol, isoamyl alcohol and other $C_4$-$C_{20}$ alcohols.

Producing Ethanol from Methanol Via Methyl Acetate

Figure 2:
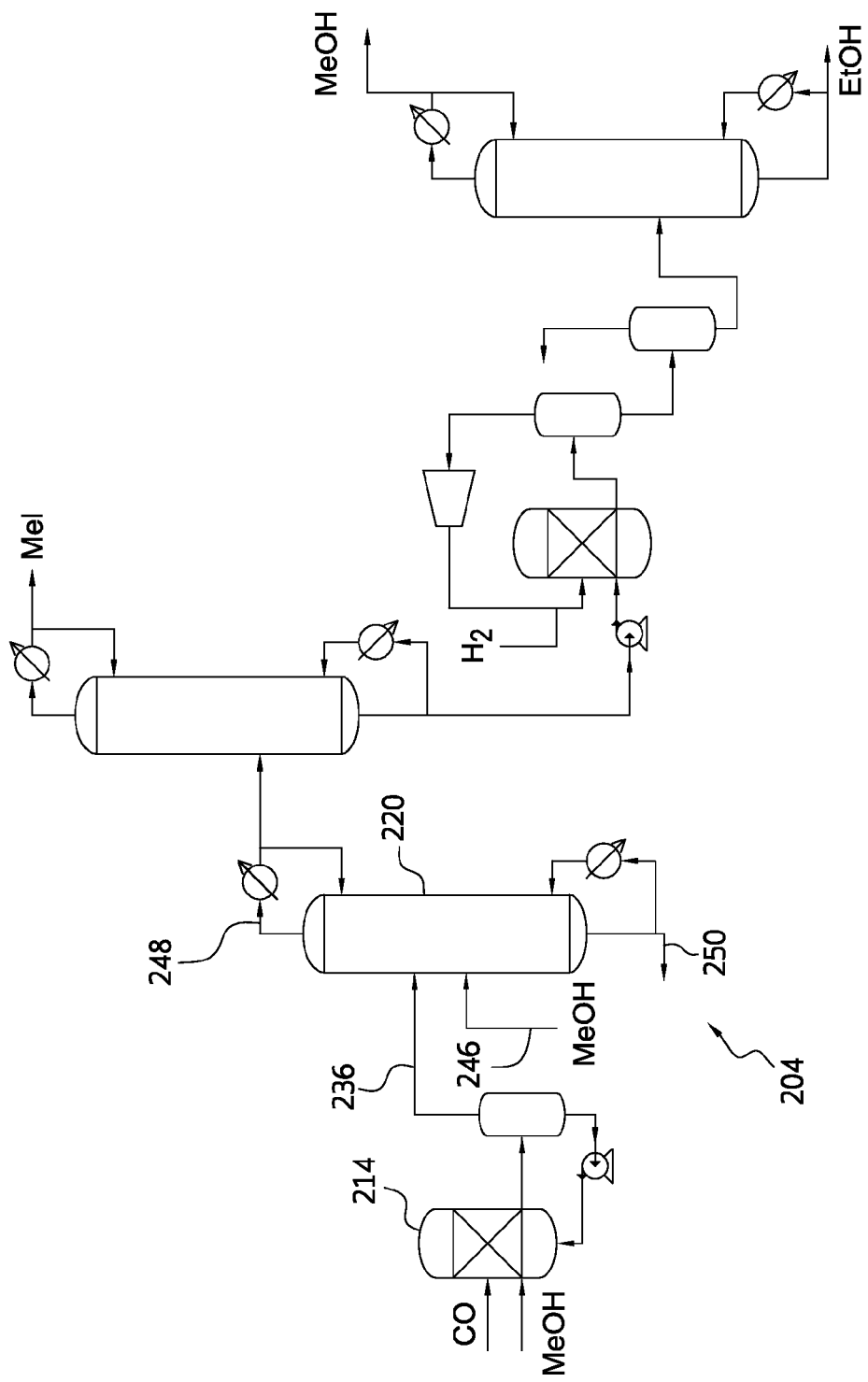
FIG. 2 is a schematic diagram of an ethanol production process that directly feds the carbonylation product to the esterification unit in accordance with one embodiment of the present invention.
Figure 3:
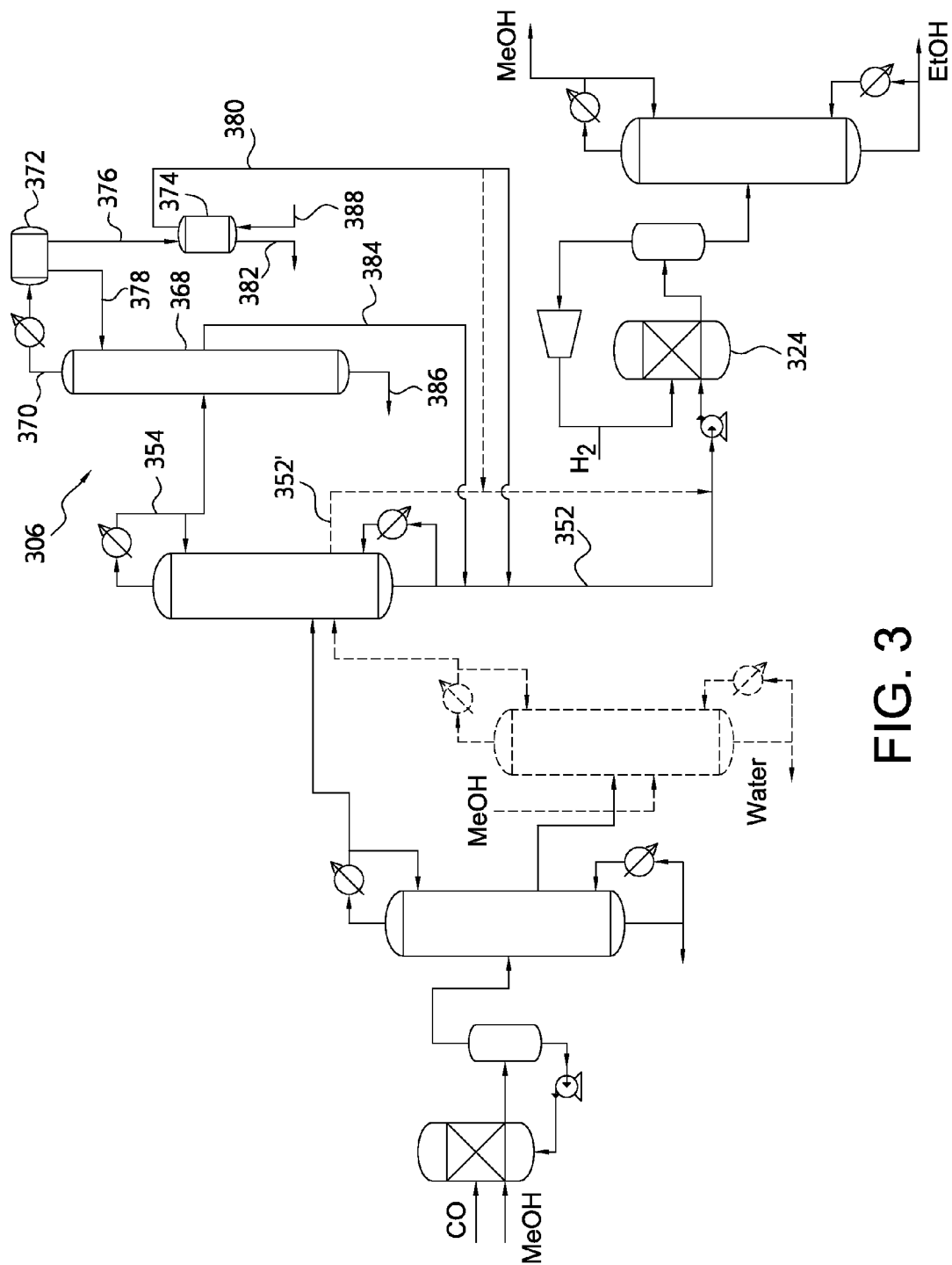
FIG. 3 is a schematic diagram of an ethanol production process with the recovery and recycle of acetaldehyde using an aqueous solvent in accordance with one embodiment of the present invention.
Figure 4:
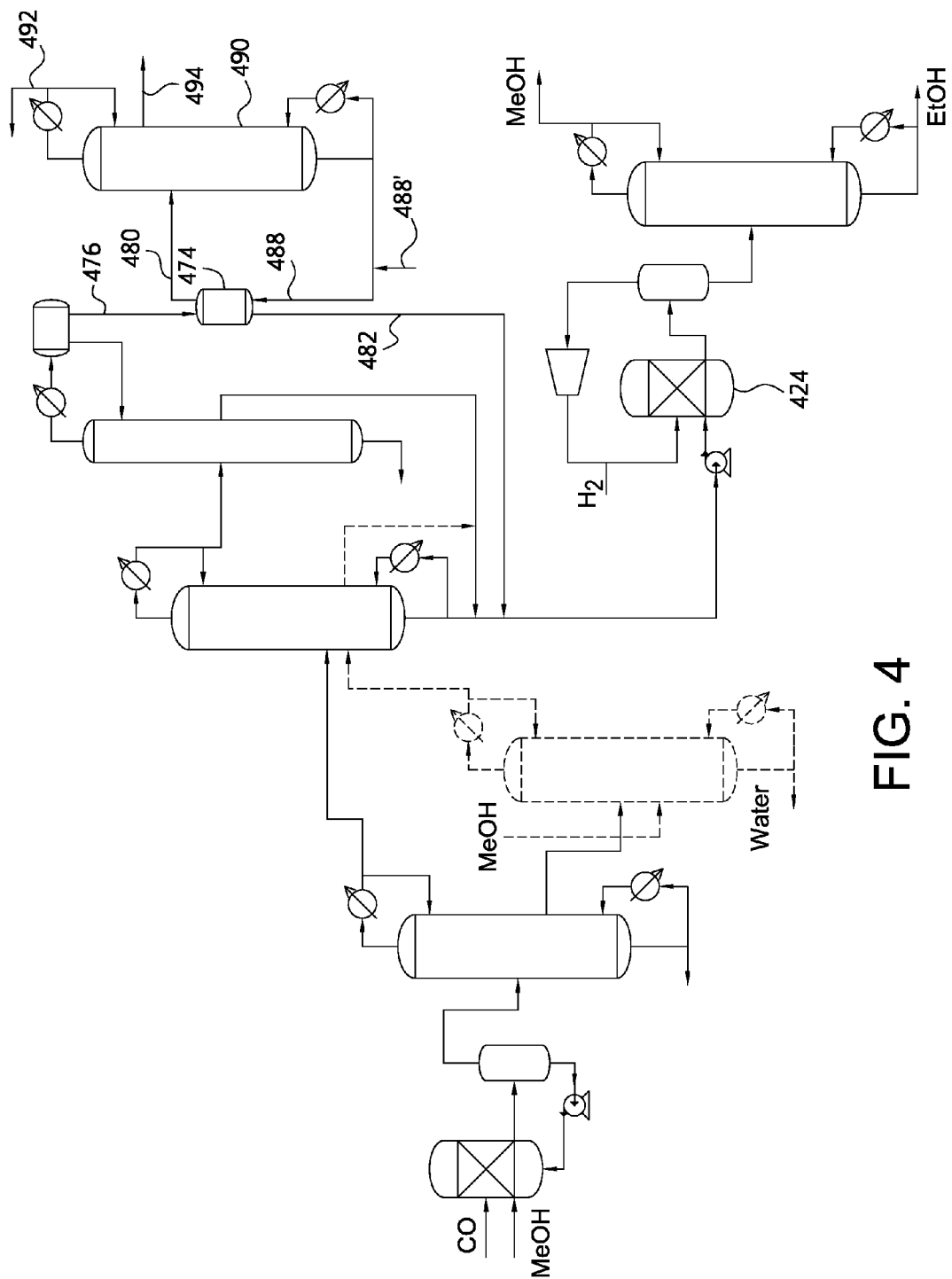
FIG. 4 is a schematic diagram of an ethanol production process with the recovery and recycle of acetaldehyde using an organic solvent in accordance with one embodiment of the present invention.

FIG. 1 shows a schematic diagram of an ethanol production process in accordance with one embodiment of the present invention. Process 100 comprises carbonylation system 102, esterification unit 104, alkyl halide removal system 106, and hydrogenolysis system 108. Carbonylation system 102 comprises reaction zone 110 and separation zone 112. Reaction zone 110 comprises carbonylation reactor 114 and flasher 116, and separation zone 112 comprises at least one distillation column 118. Esterification unit 104 comprises at least one column, e.g., a reactive distillation column 120. Alkyl halide removal system 106 comprises at least one column 122. Hydrogenolysis system 108 comprises vaporizer (not shown), hydrogenolysis reactor 124, one or more flashers 126 and column 128. FIGS. 2-4 show exemplary embodiments of the present invention. FIG. 2 shows a schematic diagram without the use of distillation column 118. FIGS. 3 and 4 show the recovery of permanganate reducing compounds (PRC's) using additional columns and extractors.

Returning to FIG. 1, in carbonylation system 102, a methanol feed stream 130 and carbon monoxide feed stream 132 are fed to a lower portion of carbonylation reactor 114. At least some of the methanol may be converted to, and hence present as, methyl acetate in the liquid reaction composition by reacting with acetic acid product or solvent. The concentration in the liquid reaction composition of methyl acetate is suitably in the range from 0.5 wt. % to 25 wt. %, e.g., from 5 wt. % to 25 wt. %, or from 10 wt. % to 24.9 wt. %.

Reactor 114 is preferably either a stirred vessel, e.g., CSTR, or bubble-column type vessel, with agitator or without an agitator, within which the reaction medium is maintained, preferably automatically, at a predetermined level. This predetermined level may remain substantially constant during normal operation. Into reactor 114, methanol, carbon monoxide, and sufficient water (not shown) may be continuously introduced as needed to maintain at least a finite concentration of water in the reaction medium. In one embodiment, carbon monoxide, e.g., in the gaseous state, is continuously introduced into reactor 114. The temperature of reactor 114 may be controlled, as indicated above. Carbon monoxide feed 132 is introduced at a rate sufficient to maintain the desired total reactor pressure.

The gaseous carbon monoxide feed is preferably thoroughly dispersed through the reaction medium by an agitator. A gaseous purge is desirably vented via an off-gas line (not shown) from reactor 114 to prevent buildup of gaseous by-products, such as methane, carbon dioxide, and hydrogen, and to maintain a carbon monoxide partial pressure at a given total reactor pressure.

The crude methyl acetate product is drawn off from reactor 114 at a rate sufficient to maintain a constant level therein and is provided to flasher 116 via stream 134. The crude methyl acetate product has the compositions as shown in Table 1.

TABLE 1

CRUDE METHYL ACETATE PRODUCT

| Component | Conc. (wt. %) | Conc. (wt. %) | Conc. (wt. %) |
| --- | --- | --- | --- |
| Methyl Acetate | 0.5 to 25 | 5 to 25 | 10 to 24.9 |
| Acetic Acid | 10 to 90 | 20 to 70 | 30 to 50 |
| Water | 5 to 40 | 5 to 30 | 10 to 30 |
| Methyl Iodide | 0.05 to 30 | 0.1 to 25 | 1 to 15 |

In flasher 116, the crude methyl acetate product is separated in a flash separation step to obtain a volatile ("vapor") overhead stream 136 comprising methyl acetate and acetic acid and a less volatile stream 138 comprising a catalyst-containing solution. Less volatile stream 138 may be also be referred to as a "liquid catalyst recycle stream." In one embodiment, overhead stream 136 may be considered as the carbonylation product, as discussed above. The catalyst-containing solution in line 138 comprises acetic acid containing the rhodium and the iodide salt along with lesser quantities of methyl acetate, methyl iodide, and water. Less volatile stream 138 preferably is recycled to reactor 114. Vapor overhead stream 136 also comprises methyl iodide, methyl acetate, acetic acid, water, and permanganate reducing compounds ("PRCs").

Overhead stream 136 from flasher 116 is directed to separation zone 112 having a first column 118. Separation zone 112 may also comprise additional units, e.g., a drying column, one or more columns for removing PRCs, heavy ends columns, extractors, etc.

In first column 118, overhead stream 136 is separated to yield a low-boiling overhead vapor stream 140, an acetic acid stream, and a high boiling residue stream 144. In one embodiment, the acetic acid product that is removed via sidestream 142 preferably is conveyed, e.g., directly, without removing substantially any water therefrom, to esterification unit 104, e.g., reactive distillation column 120 of esterification unit 104.

In one embodiment, low-boiling overhead vapor stream 140 comprises methyl acetate and methyl iodide. Low-boiling overhead vapor stream 140 may be referred to as a "first methyl acetate stream." Methyl iodide may be removed from overhead vapor stream 140 using one or more distillation columns, e.g., distillation column 122, to yield a substantially alkyl halide free methyl acetate stream 152. Low-boiling overhead vapor stream 140 may comprise other by-products, such as methanol, acetaldehyde, carbon monoxide, and hydrogen.

In one embodiment, column 118 may comprise trays having different concentrations of water. In these cases, the composition of a withdrawn sidedraw may vary throughout the column. As such, the withdrawal tray may be selected based on the amount of water that is desired, e.g., more than 0.5 wt %. In another embodiment, the configuration of the column may be varied to achieve a desired amount or concentration of water in a sidedraw. Thus, an acetic acid feed may be produced, e.g., withdrawn from a column, based on a desired water content. Accordingly, in one embodiment, the invention is to a process for producing ethanol comprising the step of withdrawing a purified acetic acid sidedraw from a distillation column in a carbonylation process, wherein a location from which the sidedraw is withdrawn is based on a water content of the sidedraw. The water content of the sidedraw may be from 20 to 70 wt. % water. The process further comprises the steps of esterifying acetic acid in the presence of methanol under conditions effective to form a methyl acetate product comprising methyl acetate and methanol, reacting methyl acetate in a hydrogenolysis reactor to form ethanol, and recovering ethanol.

The acetic acid stream in line 142, in some embodiments, comprises methyl acetate, e.g., in an amount ranging from 0.01 wt. % to 10 wt. %, e.g., from 0.1 wt. % to 8 wt. %, or from 1 wt. % to 6 wt. %. In addition to acetic acid, water, and methyl acetate, the acetic acid stream may comprise halogens, e.g., methyl iodide, which may be removed from the purified acetic acid stream.

Acetic acid stream 142 is fed to esterification system 104, e.g., reactive distillation column 122, for esterification. In some embodiments, acetic acid stream 142 may comprise at least 30 wt. % acetic acid, at least 40 wt. %, or at least 50 wt. %. In terms of ranges, the acetic acid stream optionally comprises from 30% to 95% or from 50% to 90% of the acetic acid from the crude methyl acetate product stream. The acetic acid stream may comprise from 30 to 80 wt. % acetic acid and from 20 to 70 wt. % water.

As shown in FIG. 1, acetic acid stream 142 is co-fed with methanol stream in line 146 to esterification unit 104 to form methyl acetate, thus yielding an ester enriched stream 148 comprising methyl acetate and methanol. Ester enriched stream 148 comprises methyl acetate and may be referred to as a "second methyl acetate stream." Methanol stream 146 and acetic acid stream 142 may be fed to the distillation column in a counter-current manner to facilitate the production of a reaction product. In another embodiment, not shown, methanol stream 146 may be added directly to acetic acid stream 142 prior to being introduced into esterification unit 104.

Although expressed as column 120 in FIG. 1, in some embodiments, esterification unit 104 comprises a reaction zone comprising a reactor, coupled to a separation zone comprising one or more distillation columns and/or stripping columns. Suitable reactors for use in the esterification include batch reactors, continuously-fed stirred-tank reactors, plug-flow reactors, reactive distillation towers, or a combination thereof. An acid catalyst may be fed to the reactor to facilitate the esterification of the acetic acid. Suitable acid catalysts for use in the present invention include, but are not limited to sulfuric acid, phosphoric acid, sulfonic acids, heteropolyacids, other mineral acids and a combination thereof.

In one embodiment, second column 120 comprises an ion exchange resin bed, an acidic catalyst, or combinations thereof. Non-limiting examples of ion exchange resins suitable for use in the present invention include macroporous strong-acid cation exchange resins such as those from the Amberlyst® series distributed by Rohm and Haas. Additional ion exchange resins suitable for use in the present invention are disclosed in U.S. Pat. Nos. 4,615,806, 5,139,981, and 7,588,690, the disclosures of which are incorporated by reference in their entireties. Second column 120 may comprise an acid selected from the group consisting of sulfuric acid, phosphoric acid, sulfonic acids, heteropolyacids, other mineral acids and a combination thereof. In other embodiments, acid catalysts include zeolites and supports treated with mineral acids and heteropolyacids.

The operating parameters of esterification unit 104 may be varied to achieve a desired composition in ester enriched stream 148. For example, temperature, pressure, feed rates, and residence times can be varied to increase conversion of acetic acid to an ester, decrease the formation of impurities, achieve more efficient separation, reduce energy consumption, or combinations thereof.

In one embodiment, esterification unit 104 operates at a base temperature from 100° C. to 150° C., e.g., from 100° C. to 130° C. In terms of pressure, esterification unit 104 may be operated at atmospheric pressure, subatmospheric pressure, or superatmospheric pressure. For example, esterification unit 104 operates at a pressure from 50 kPa to 500 kPa, e.g., from 50 kPa to 400 kPa.

In some embodiments, the feed rates of acetic acid and methanol to the esterification unit 104 may be adjusted to control the mole ratio of acetic acid to methanol being fed to esterification unit 104. For example, the mole ratio of acetic acid to methanol fed to esterification unit 118 is from 1:1 to 1:15, e.g., from 1:1 to 1:5, or from 1:1 to 1:2.

The processes of the present invention preferably provide for a high conversion of acetic acid to ester(s). In some embodiments, for example, at least 80%, at least 90% or at least 95% of the acetic acid in acetic acid stream 142 is converted to an ester.

Ester enriched stream 148 exiting esterification unit 104 preferably comprises at least 60 wt. % methyl acetate, e.g., at least 70 wt. % or more preferably at least 75 wt. %. In terms of ranges, ester enriched stream 148 may comprise at least methyl acetate in an amount from 40 to 99 wt. %, e.g., from 50 to 90 wt. % or from 65 to 90 wt. %.

When excess methanol is reacted with the acetic acid from acetic acid stream 142, some methanol may be present in ester enriched stream 148. Thus, ester enriched stream 148 may comprise methanol in an amount from 0.1 to 80 wt. %, e.g., from 1 to 60 wt. %, or from 10 to 30 wt. %. In other embodiments, where the acetic acid is present in an excess relative to methanol or where the acetic acid is present in about the same molar amount as methanol, ester enriched stream 148 may be substantially free of methanol, e.g., containing less than 10 wt. %, less than 5 wt. % or less than 1 wt. %.

Methyl acetate in stream 148 may be removed from esterification unit 104 and fed directly, or combined with low-boiling overhead vapor stream 140, to distillation column 122. As a result of esterification, the total conversion of acetic acid, may be greater than 90%, e.g., greater than 95% or greater than 99%. As a result of esterification, a water stream in line 150 may be recovered with high purity. In some embodiments, water stream 150 may be separated from ester enriched stream 148 in the residue. Preferably, water stream 150 comprises little, if any, unreacted acetic acid, which may be further neutralized, and/or separated from water stream 150. In some embodiments, water stream 150 may comprise little, if any acetic acid, e.g., containing less than 5 wt. % acetic acid, and more preferably less than 1.5 wt. % acetic acid.

As stated above, acetic acid stream in line 142 may comprise hydrogen iodide. For example, acetic acid stream in line 142 may comprise less than 5 wt. % HI, e.g., less than 1 wt. % or less than 0.5 wt. %. HI may be fed to reactive distillation column 120 along with acetic acid, water and methyl acetate. In some embodiments, a minor amount of methyl iodide may also be fed to reactive distillation column 120. Any HI in reactive distillation column 120 may be converted to MeI and removed in distillate 148. In addition, HI may beneficially act as a catalyst to promote the esterification of acetic acid to methyl acetate. Therefore, the need to add corrosive metals, such as sulfuric acid, may be reduced or eliminated depending the concentration of HI.

Embodiments of the present invention beneficially generate additional methyl acetate from acetic acid to increase the yield of the final product ethanol. The esterification of acetic acid with methanol increases the overall raw material efficiency by at least 5% relative to the same system but without an esterification unit.

As shown, ester enriched stream 114 is combined with low-boiling overhead vapor stream 140 and co-fed to distillation column 122 to recover a substantially alkyl halide-free methyl acetate stream 152 in the residue. The substantially alkyl halide-free methyl acetate stream 152 may also be referred to as a "third methyl acetate stream." In one embodiment, ester enriched stream 114 and low-boiling overhead vapor stream 140 may be fed separately to distillation column 122.

Returning to first column 118, low-boiling overhead vapor stream 140 and ester enriched stream 148 is directed to distillation column 122, which serves to form an alkyl halide enriched distillate 154, which is also enriched in PRC's, notably acetaldehyde, due to the similar boiling points of alkyl halide, e.g., methyl iodide, and PRC's, acetaldehyde. Preferably, alkyl halide enriched distillate 154 comprises most of the alkyl halide in low-boiling overhead vapor stream 140 and ester enriched stream 148. In one embodiment, streams 140 and 142 are introduced in the lower part of distillation column 122, e.g., lower half or lower third. Distillation column 122 removes alkyl halides and PRC's, as the distillate in line 154. Alkyl halide enriched distillate 154 preferably is refluxed, for example, at a reflux ratio from 1:10 to 10:1. Distillation column 122 is preferably a tray column as described above and preferably operates at atmospheric pressure. The temperature of the alkyl halide enriched distillate exiting in line 154 from distillation column 122 preferably is from 0° C. to 70° C., e.g., from 10° C. to 50° C. The temperature of the residue exiting from column 122 preferably is from 60° C. to 115° C., e.g., from 70° C. to 110° C.

In one embodiment, alkyl halide enriched distillate 154 comprises at least 95% of the alkyl halide in streams 140 and 142, e.g., at least 98 wt. %, or at least 99.5 wt. %. In some embodiments, alkyl halide enriched distillate 154 comprises methyl acetate. Methyl acetate and PRC's in alkyl halide enriched distillate 154 may be recovered and react with hydrogen to generate additional ethanol product.

The substantially alkyl halide-free methyl acetate stream 152 is withdrawn from distillation column 122 and fed to hydrogenolysis system 108. Preferably, methyl acetate stream 152 comprises methyl acetate and methanol from low-boiling overhead vapor stream 140 and ester enriched stream 148. In one embodiment, methyl acetate stream 152 comprises greater than 50 wt. % methyl acetate, greater than 60 wt. %, or greater than 70 wt. %.

Methyl acetate stream comprises methyl acetate and methanol in line 152 is directed to the hydrogenolysis zone 108. Methyl acetate stream 152 may be vaporized via a vaporizer (not shown) and co-fed with hydrogen in line 156 to hydrogenolysis reactor 124. Optionally, methyl acetate stream 152 may be withdrawn from column 122 as a vapor stream and be fed directly to hydrogenolysis reactor 124 without the use of a vaporizer. In addition, methyl acetate stream in line 152 may also be pre-heated before being fed to hydrogenolysis reactor 124. Methyl acetate stream 152 and hydrogen in line 156 may be preheated to a temperature of at least 150° C., e.g., at least 200° C., before being fed to hydrogenolysis reactor 124, provided that the feed remains in the vapor phase and above the dew point.

Hydrogenolysis reactor 124 preferably comprises a hydrogenolysis catalyst. The reactants, namely the methyl acetate in the methyl acetate of column 122, react in the presence of hydrogen and the catalyst to form methanol. Suitable hydrogenolysis catalysts include copper support on silica or copper oxide supported on magnesia-silica, Raney copper catalysts, and Group VIII supported catalysts. Further catalysts are described in U.S. Pat. No. 5,198,592, and Claus, et al., "Selective Hydrogenolysis of methyl and ethyl acetate in the gas phase on copper and supported Group VIII metal catalysts," Applied Catalysts A: General, Vol. 79 (1991) pages 1-18, which are incorporated herein by reference. The reduction of methyl acetate to produce ethanol, e.g., in the hydrogenolysis reactor, is typically conducted at elevated temperatures from 125° C. to 350° C., e.g., from 180° C. to 345° C., from 225° C. to 310° C. The pressure in the hydrogenolysis reactor may operate under high pressure of greater than 1000 kPa, e.g., greater than 3,000 kPa or greater than 5,000 kPa. In terms of ranges the pressure in the hydrogenolysis reaction may be from 700 to 8,500 kPa, e.g., from 1,500 to 7,000 kPa, or from 2,000 to 6,500 kPa. Pressure greater than 2,500 kPa is more favorable for improving ethanol productivity and/or selectivity. The reactants may be fed to hydrogenolysis reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. The hydrogenolysis reaction may be conducted with excess molar amounts of hydrogen and preferably the molar ratio of hydrogen to methyl acetate is greater than 10:1, e.g., greater than 15:1, or greater than 20:1. In one preferred embodiment, the molar ratio is about 25:1.

The crude reaction product of hydrogenolysis reactor 124 is continuously withdrawn via line 158. In one embodiment, the crude reaction product comprises at least 5% less methyl acetate than the methyl acetate stream in line 152, e.g., at least 75% less methyl acetate or at least 90% less methyl acetate. The crude reaction product of hydrogenolysis reactor 124 may comprise at least 5% more methanol than the methanol in line 152, e.g., at least 10% more methanol, or at least 25% more methanol. Methanol and ethanol are the primary products of the hydrogenolysis reaction, and the crude reaction product comprises at least 15 wt. % methanol and at least 15 wt. % ethanol, e.g., at least 20 wt. %, or at least 25 wt. %. In addition, depending on conversion, the crude reaction product comprises less than 20 wt. % methyl acetate, e.g. less than 15 wt. %, or less than 10 wt. %. Other components, such as water, hydrogen, acetaldehyde, and other impurities may be present in the crude product of hydrogenolysis reactor 124 in minor amounts.

The crude reaction product in line 158, which may be referred to as a crude ethanol product, may be condensed and fed to separator 126, which, in turn, provides a vapor stream and a liquid stream. Separator 126, e.g., a flasher or knock-out pot, in one embodiment operates at a temperature from 50° C. to 500° C. and a pressure from 50 kPa to 2,000 kPa. In an embodiment, one or more separators may be used to condense the crude reaction product.

The vapor stream exiting separator 126 may comprise hydrogen and hydrocarbons, which may be purged and/or returned to hydrogenolysis reactor 124 via line 160. As shown in FIG. 1, the returned portion of the vapor stream in line 160 is combined with the fresh hydrogen in line 156. In another embodiment, the fresh hydrogen in line 156 may passes through compressor 126 along with hydrogen vapor stream 160. In another embodiment, fresh hydrogen in line 156 and vapor stream in line 160 may be fed separately into hydrogenolysis reactor 124.

The liquid stream exiting separator 126 comprises ethanol and methanol, and may have some unreacted methyl acetate. As shown in FIG. 1, the liquid stream in line 162 is fed to column 128 to recover ethanol. Liquid stream 162 from separator 126 is fed to column 128, also referred to as the "product column." More preferably, the liquid stream in line 162 is introduced in the middle part of product column 128. Product column 128 recovers ethanol, which preferably is substantially pure other than the azeotropic water content, as the residue in line 166. Distillate in line 164, which preferably comprises methanol and methyl acetate, is preferably removed and may be recycled to esterification column 120 to generate additional methyl acetate to be converted into ethanol. The distillate of product column 128 preferably is refluxed, for example, at a reflux ratio from 1:10 to 10:1. Product column 128 is preferably a tray column as described above and preferably operates at atmospheric pressure. The temperature of the distillate exiting in line 164 from product column 128 preferably is from 30° C. to 100° C., e.g., from 40° C. to 90° C. The temperature of the third residue exiting from product column 128 preferably is from 60° C. to 110° C., e.g., from 70° C. to 100° C. Exemplary components of the distillate and residue compositions for product column 128 are provided in Table 2 below. It should be understood that the distillate and residue may also contain other components, not listed, such as components in the feed.

TABLE 2

PRODUCT COLUMN

|  | Conc. (wt. %) | Conc. (wt. %) | Conc. (wt. %) |
|---|---|---|---|
| Distillate | | | |
| Ethanol | <2 | <1 | 0.01 to 1 |
| Methanol | <60 | 70 to 95 | 80 to 90 |
| Methyl Acetate | 1 to 40 | 1 to 30 | 10 to 20 |
| Residue | | | |
| Ethanol | >70 | 80 to 99.9 | 90 to 99 |
| Water | <12 | 1 to 9 | 3 to 8 |
| Methanol | <1 | 0.001 to 1 | 0.05 to 0.5 |

In another embodiment, overhead stream 136 from flasher 116 may be fed directly to esterification unit 104. As shown in FIG. 2, overhead stream 236, which comprises methyl acetate and acetic acid, bypasses the first column and is fed directly to esterification unit 204 along with excess methanol via line 246 to form a methyl acetate enriched stream. The methyl acetate enriched stream is recovered from esterification unit 204, e.g., reactive distillation column 220, in line 248. Methyl acetate enriched stream 248 comprises methyl acetate generated in carbonylation reactor 214 and methyl acetate generated in esterification unit 204. In one embodiment, the methyl acetate enriched stream comprises greater than 50 wt. % methyl acetate, e.g., greater than 60 wt. %, or greater than 70 wt. %. In one embodiment, the methyl acetate enriched stream comprises at most 86 wt. % methyl acetate, e.g., at most 82 wt. %, or at most 80 wt. %. In addition, methyl acetate enriched stream 248 also comprises methanol, alkyl halide, i.e., methyl iodide, PRC's, and other side products.

The light end column in FIG. 1 is used to remove a large portion of water from the reaction. As such, some of the acetic acid is also removed in the residue and therefore reducing the amount of acetic acid that is fed to the esterification unit from the sidestream. In accordance with the embodiment as illustrated in FIG. 2, all of the acetic acid generated in the carbonylation unit is fed to esterification unit 204. Therefore, more methyl acetate may be generated, which in turn beneficially increases the overall production of ethanol.

Any unreacted acetic acid, along with water, may be removed in residue stream 250, In one embodiment, portions of residue stream 250 may be returned to carbonylation system 202 to regulate the water level for the carbonylation system.

As stated above, byproducts such as PRC's, i.e., acetaldehyde, may be formed during the carbonylation reaction. In an embodiment of the present invention, PRC's is recovered from the alkyl halide enriched stream and may be fed to the hydrogenolysis reactor to form ethanol. As shown in FIG. 3, alkyl halide enriched distillate 154 is fed to permanganate recovery system (PRS) 306 to recover the PRC's.

As shown in FIG. 3, alkyl halide enriched stream 354 is directed to distillation column 368, which serves to form a vapor phase 370 enriched in PRC's, i.e., acetaldehyde, but also containing alkyl halide, i.e., methyl iodide, due to the similar boiling points of methyl iodide and acetaldehyde. Vapor phase 370 is condensed and then extracted with water to recover PRC's. In a preferred embodiment, a portion of vapor stream 370 is provided as reflux to distillation column 368. This can be accomplished, as shown in FIG. 3, by providing vapor stream 370 to an overhead receiver 372, from which a portion of vapor stream 370 can be provided to extraction unit 374 by light phase stream 376 and another portion of vapor stream 370 can be provided as reflux to distillation column 368 by stream 378.

Acetaldehyde may be extracted by water to obtain aqueous acetaldehyde stream 380, which may be fed to the hydrogenolysis reactor to make ethanol. In one embodiment, aqueous acetaldehyde stream 380 may be fed directly to hydrogenolysis reactor 324, or may be co-fed to hydrogenolysis reactor 324 with methyl acetate stream 352. In one embodiment, each or both of streams 380 and 352 may be vaporized in a vaporizer prior to being fed to hydrogenolysis reactor 324.

In another embodiment, a drying column may be used to remove water from the acetaldehyde stream to yield a substantially water free acetaldehyde stream. This acetaldehyde stream may be vaporized by a vaporized methyl acetate stream in line 352'. The combined vaporized stream may be fed directly to hydrogenolysis reactor 324 without the need of a vaporizer.

The raffinate in line 382 from extraction unit 374, notably containing methyl iodide is desirably returned to the carbonylation process.

In another embodiment of the present invention, distillation column 368 separates alkyl halide enriched stream 354 into vapor stream 370, a higher boiling liquid phase residuum stream 386, and sidestream 384, which comprises methyl acetate.

Sidestream 384 allows distillation column 368 to be operated under conditions desirable for obtaining a higher concentration of acetaldehyde in vapor stream 370 while providing a mechanism for removing methyl acetate that might otherwise build up in the center of distillation column 368 or be pushed into vapor phase stream 370. Sidestream 384 comprises at least 80 wt. % methyl acetate, e.g., at least 90 wt. % or at least 95 wt. %. In one embodiment, sidestream 384 is in vapor phase. Therefore, aqueous acetaldehyde stream 380, or a substantially water-free acetaldehyde stream, may be vaporized by methyl acetate sidestream 384 and be co-fed to hydrogenolysis reactor 324.

In this embodiment, vapor stream 370 is enriched with PRC, notably acetaldehyde, with respect to alkyl halide enriched stream 354. Vapor stream 370 is deficient with methyl acetate, methanol, and/or acetic acid (desirably all three) with respect to alkyl halide enriched stream 354. Vapor stream 370 is deficient with methyl acetate, methanol, and/or acetic acid (desirably all three) with respect to sidestream 384 and, desirably, also with respect to higher boiling liquid phase residuum stream 386. Desirably, vapor stream 370 is enriched with PRC, notably acetaldehyde, with respect to both sidestream 384 and higher boiling liquid phase residuum stream 386.

In another embodiment, the alkyl halide is extracted from light phase stream 476 with an organic extractant. Preferably, the organic extractant is selected is selected from the group consisting of $C_6$ to $C_{16}$ alkanes and combinations thereof. As a result of this extraction, light phase 476 is separated into an extractant stream 480 comprising the extractant and alkyl halide, and a raffinate 482 comprising methyl acetate and PRC's.

Accordingly, it is desirable that the extraction be conducted at a combination of temperature and pressure such that the extractor contents can be maintained in the liquid state. In some embodiments, extraction is conducted at a temperature from 10° C. to 40° C.

Although the specific compositions of extract stream 480 may vary widely, it is preferred that a majority of the alkyl halides in light phase 476 pass through to extract stream 480. In one embodiment, at least 70% of the alkyl halides in light phase 476 pass through to extract stream 480, e.g., more preferably at least 85% or at least 95%. In a preferred embodiment, about 99% or more of the alkyl halides in light phase 476 pass through to the extract stream 480. When methyl iodide is present in light phase 476, at least 70% of the methyl iodide passes through to extract stream 480, e.g., more preferably at least 85% or at least 95%. In addition, extract stream 480 preferably comprises a low weight percent of PRC's, e.g., less than 10 wt. % of the total weight of extract stream 480 comprises PRC's, or more preferably less than 5 wt. %. In one embodiment, extract stream 480 preferably comprises substantially no PRC's and the PRC's in light phase 476 pass through to raffinate stream 482.

Raffinate stream 482 comprises PRC's, i.e., acetaldehyde, and is fed directly or indirectly to hydrogenolysis reactor 424 to make ethanol. In addition, raffinate stream 482 from extractor 474 may comprise methyl acetate and water. Although the specific compositions may vary widely, raffinate stream 482 preferably comprises less than 2 wt. % of the halogen promoter and/or $C_{2+}$ alkyl halides, e.g., less than 1 wt. % or less than 0.5 wt. %, or less than 0.1 wt. %.

Extract stream 480 is directed to removal column 490 to produce a distillate stream 492 comprising halogen promoter and/or $C_{2+}$ alkyl halides, and a residue stream 488 comprising the extractant. Residue stream 488 may be cooled and recycled directly to extractor 474, or preferably is combined with extractant feed stream 488' and fed to extractor 474.

Distillate stream is condensed and returned to the process via stream 492. At least a portion of the condensed distillate stream is refluxed back to the removal column. Distillate stream 492 primarily comprises halogen promoter.

In some embodiments, an alkyl halide purge stream 494 can be taken from removal column 490. Alkyl halide purge stream 494 comprises one or more $C_{2+}$ alkyl halides selected from the group consisting of ethyl iodide, propyl iodide, butyl iodide, pentyl iodide, hexyl iodide, and isomers and mixtures thereof. In some embodiments, $C_{2+}$ alkyl halides purge stream 494 is directed to a holding tank and stored (not shown). Optionally, $C_{2+}$ alkyl halides purge stream 494 can be further processed to recover any halogen promoters or iodine value, such as HI, contained in the purge stream, wherein the halogen promoter or iodine value is returned to the process.

As a result of recovering additional methyl acetate and PRC's from the alkyl halide enriched streams as illustrated in FIGS. 3 and 4, the overall all production of ethanol is increased.

Ethanol Composition

The ethanol product made using the embodiments of the present invention may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 3.

TABLE 3

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 850 wppm, or from 100 to 700 wppm. In one embodiment, the finished ethanol composition is substantially free of acetaldehyde, optionally comprising less than 8 wppm acetaldehyde.

In some embodiments, when further water separation is used, the ethanol product may be withdrawn as a stream from the water separation unit such as an adsorption unit, membrane, molecular sieve, or extractive distillation column. Ethanol concentration of the ethanol product may be higher than indicated in Table 7, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstock, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid catalysts, can be employed to dehydrate ethanol, as described in U.S. Pub. Nos. 2010/0030002 and 2010/0030001 and WO2010146332, the entire contents and disclosures of which are hereby incorporated by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

EXAMPLE

Example 1

Multiple simulations of processes under different catalyst performances in accordance with FIG. 1 were completed using ASPEN™ software. In each stream, the flow rate and composition vary with the catalyst performance and design specifications. In general, an illustrative composition for the various process streams is demonstrated in Table 4 based upon the simulation results. For simplicity, the composition of a component in Table 4 is displayed as 0% if its level is so low that it becomes hardly detectable. For simplicity, the composition of a component in Table 4 is displayed as 100% if other components are so low and hardly detectable.

TABLE 4

SIMULATED COMPOSITIONAL DATA FOR PROCESS STREAMS

| | Composition (wt. %) | | | | | | | | |
|---|---|---|---|---|---|---|---|---|---|
| | MeOAc | HOAc | MeOH | EtOH | H$_2$O | MeI | Heavies | AcH | Other |
| Carbonylation Reaction Zone | | | | | | | | | |
| Crude Methyl Acetate Stream 134 | 24.9 | 42.4 | 3 | — | 11.1 | 10.6 | 7 | | 1 |
| Overhead stream 136 First Column | 40.9 | 19 | 4.1 | | 10.4 | 24.1 | 0 | | 1.5 |
| Vapor Stream 140 | 44.6 | 0 | 3.1 | | 1.8 | 39.7 | | | |
| Sidestream 142 Esterification Zone | 5.4 | 59.6 | 5.2 | | 29.3 | 0 | | | |
| Ester Enriched Stream 148 | 76.5 | 0 | 23.4 | | 0.1 | | | | |
| Reside Stream 150 Alkyl Halide Removal System | 0 | 1.4 | 0 | | 97.8 | | | | |
| Distillate 154 | 2.5 | 0 | 5.6 | | 0 | 86.8 | | 0.4 | |
| Methyl Acetate Stream 152 Hydrogenolysis System | 86.2 | 0 | 11.4 | | 2.4 | 0 | | 0 | |
| Distillate 164 | 15 | | 83.4 | 0 | 0 | | | | |
| Residue 166 | 0 | | 0 | 93.6 | 4.4 | | | | |

As shown by the table above, methyl acetate may be used to make ethanol through hydrogenolysis, where the methyl acetate is obtained through carbonylation of methanol and carbon monoxide and esterification of acetic acid and methanol. The process produces a final ethanol product with less than 5 wt. % water.

We claim:

1. A process for producing ethanol by hydrogenolysis of methyl acetate comprising:
   reacting carbon monoxide and methanol in a reaction medium to form a reaction solution that comprises acetic acid and from 0.5 to 25 wt. % methyl acetate, wherein the reaction medium comprises water, acetic acid, methyl acetate, a first catalyst, and an alkyl halide;
   flashing the reaction solution to yield a carbonylation product and a liquid catalyst recycle stream;
   separating the carbonylation product into a first methyl acetate stream and an acetic acid stream;
   esterifying the acetic acid stream to form a second methyl acetate stream;
   feeding the first methyl acetate stream and the second methyl acetate stream to a distillation column to remove alkyl halides and obtain a third methyl acetate stream;
   reacting the third methyl acetate stream and hydrogen in the presence of a second catalyst to form an alcohol product that comprises ethanol and methanol; and
   recovering ethanol from the alcohol product.

2. The process of claim 1, wherein the third methyl acetate stream comprises at least 60 wt. % methyl acetate.

3. The process of claim 1, wherein the third methyl acetate stream comprises less than 5 wt. % acetic acid.

4. The process of claim 1, wherein the third methyl acetate stream is substantially free of methyl iodide.

5. The process of claim 1, further comprising withdrawing the acetic acid as a sidedraw.

6. The process of claim 5, wherein the sidedraw comprises at least 30 wt. % acetic acid.

7. The process of claim 5, wherein the sidedraw comprises less than 10 wt. % methyl acetate.

8. The process of claim 5, wherein the sidedraw comprises less than 0.1 wt. % alkyl halide.

9. The process of claim 1, wherein the first methyl acetate stream comprises at least 20 wt. % methyl acetate.

10. The process of claim 1, wherein the second methyl acetate stream comprises at least 50 wt. % methyl acetate.

11. The process of claim 1, wherein the second methyl acetate stream comprises less than 5 wt. % acetic acid.

12. The process of claim 1, wherein the second methyl acetate stream comprises less than 2 wt. % water.

13. The process of claim 1, further comprising esterifying the acetic acid stream with methanol in a reactive distillation column.

14. The process of claim 13, further comprising separating a water stream from the reactive distillation column.

15. A process for producing ethanol by hydrogenolysis of methyl acetate comprising:
    reacting carbon monoxide and methanol in a reaction medium to form a reaction solution that comprises acetic acid and from 0.5 to 25 wt. % methyl acetate, wherein the reaction medium comprises water, acetic acid, methyl acetate, a first catalyst, and an alkyl halide;
    flashing the reaction solution to yield a carbonylation product and a liquid catalyst recycle stream, wherein the carbonylation product comprises acetic acid and methyl acetate;
    esterifying the carbonylation product to form a methyl acetate enriched stream;
    feeding the methyl acetate enriched stream to a distillation column to form an alkyl halides stream and a methyl acetate stream;
    reacting the methyl acetate stream and hydrogen in the presence of a second catalyst to form an alcohol product that comprises ethanol and methanol; and
    recovering ethanol from the alcohol product.

16. A process for producing ethanol by hydrogenolysis of methyl acetate comprising:
    reacting carbon monoxide and methanol in a reaction medium to form a reaction solution that comprises acetic acid, acetaldehyde, and methyl acetate, wherein the reaction medium comprises water, acetic acid, a first catalyst, and an alkyl halide;
    flashing the reaction solution to yield a carbonylation product and a liquid catalyst recycle stream;
    separating the carbonylation product into an acetic acid stream and a first overhead stream comprising methyl acetate, acetaldehyde, and alkyl halide;
    separating the first overhead stream into a methyl acetate residue and a second overhead stream comprising acetaldehyde and alkyl halide;
    extracting the second overhead stream with an aqueous stream to obtain a raffinate comprising alkyl halide and an extractant comprising acetaldehyde;
    combining the methyl acetate residue and extractant to form a feed stream;
    reacting the feed stream and hydrogen in the presence of a second catalyst to form an alcohol product that comprises ethanol and methanol; and
    recovering ethanol from the alcohol product.

17. The process of claim 16, further comprising esterifying the acetic acid stream to form a methyl acetate stream and introducing the methyl acetate stream with the first overhead stream prior to separation.

18. A process for producing ethanol by hydrogenolysis of methyl acetate comprising:
    reacting carbon monoxide and methanol in a reaction medium to form a reaction solution that comprises acetic acid, acetaldehyde, and methyl acetate, wherein the reaction medium comprises water, acetic acid, a first catalyst, and an alkyl halide;
    flashing the reaction solution to yield a carbonylation product and a liquid catalyst recycle stream;
    separating the carbonylation product into an acetic acid stream and a first overhead stream comprising methyl acetate, acetaldehyde, and alkyl halide;
    separating the first overhead stream into a methyl acetate residue and a second overhead stream comprising acetaldehyde and alkyl halide;
    extracting the second overhead stream with an alkane to obtain a raffinate comprising acetaldehyde and an extractant comprising the alkyl halide and alkane;
    combining the methyl acetate residue and the raffinate to form a feed stream;
    reacting the feed stream and hydrogen in the presence of a second catalyst to form an alcohol product that comprises ethanol and methanol; and
    recovering ethanol from the alcohol product.

19. The process of claim 18, further comprising esterifying the acetic acid stream to form a methyl acetate stream and introducing the methyl acetate stream with the first overhead stream prior to separation.

20. The process of claim 18, wherein the alcohol product is free of water.

21. The process of claim 18, wherein the ethanol comprises less than 1 wt. % water.

\* \* \* \* \*